(12) United States Patent
Williams et al.

(10) Patent No.: US 10,993,767 B2
(45) Date of Patent: May 4, 2021

(54) MICROWAVE ABLATION ANTENNA ASSEMBLIES

(71) Applicant: Gyrus Medical Limited, Cardiff (GB)

(72) Inventors: David Nicholas Williams, Caerphilly (GB); Tudor Thomas, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 55 days.

(21) Appl. No.: 15/429,626

(22) Filed: Feb. 10, 2017

(65) Prior Publication Data

US 2017/0231696 A1 Aug. 17, 2017

(30) Foreign Application Priority Data

Feb. 11, 2016 (GB) ..................................... 1602446

(51) Int. Cl.
*A61B 18/18* (2006.01)
*A61B 18/00* (2006.01)

(52) U.S. Cl.
CPC ...... *A61B 18/1815* (2013.01); *A61B 2018/00577* (2013.01); *A61B 2018/183* (2013.01); *A61B 2018/1823* (2013.01); *A61B 2018/1838* (2013.01); *A61B 2018/1892* (2013.01)

(58) Field of Classification Search
CPC ............... A61B 18/18; A61B 18/1815; A61B 2018/00577; A61B 2018/1823; A61B 2018/183; A61B 2018/1838; A61B 2018/1892
USPC .............................. 606/33–50; 607/154, 156
See application file for complete search history.

(56) References Cited

U.S. PATENT DOCUMENTS

| 2002/0022836 A1* | 2/2002 | Goble ............. A61B 18/042 606/34 |
| 2006/0155270 A1* | 7/2006 | Hancock ........ A61B 18/18 606/33 |
| 2011/0208177 A1* | 8/2011 | Brannan ......... A61B 18/18 606/33 |
| 2011/0282336 A1* | 11/2011 | Brannan ......... A61B 18/1815 606/33 |

FOREIGN PATENT DOCUMENTS

| EP | 2060239 A1 | 5/2009 |
| EP | 2158868 A1 | 3/2010 |
| EP | 2485326 A1 | 8/2012 |

OTHER PUBLICATIONS

Parker, Dr. Matthew, "Combined Search and Examination Report", prepared for GB1602446.5, dated Jul. 18, 2016, 5 pages.

* cited by examiner

*Primary Examiner* — Michael F Peffley
*Assistant Examiner* — Khadijeh A Vahdat
(74) *Attorney, Agent, or Firm* — Winstead PC

(57) ABSTRACT

A microwave ablation antenna assembly includes an elongate body that extends from a first end to a second end thereof, and which defines therein a hollow inner volume and a longitudinal axis of the antenna. The ablation antenna assembly includes an applicator tip portion mounted on the second end of the elongate body, an elongate coaxial conductor assembly for connection to a source of microwave energy, a dipole tip portion that extends from the feed point of the coaxial conductor assembly towards the applicator tip, and a choke assembly with first and second choke conductors.

11 Claims, 4 Drawing Sheets

MICROWAVE ABLATION ANTENNA ASSEMBLIES

FIELD OF THE INVENTION

The present invention relates to microwave ablation antenna assemblies.

BACKGROUND OF THE INVENTION

In the treatment of tumours, for example tumours caused by a disease such as cancer, it is known to use microwave ablation techniques to ablate the tumour. Such microwave ablation techniques typically ablate the targeted tissue by delivering a controlled amount of microwave energy into the tumour.

Minimally-Invasive techniques for delivering such microwave energy have been shown to be effective in the treatment of tumours. In a minimally-invasive technique, a microwave emitter is inserted directly into a point of treatment, either using a normal body orifice or via percutaneous insertion. Such minimally-invasive procedures and devices provide a means of treating tumours in patients who either cannot undergo other forms of treatment (e.g. radiotherapy, surgical resection, chemotherapy) or where ablation is preferred as a therapy.

One type of commonly used microwave antenna assembly includes a dipole antenna, which consists of a coaxial construction having an inner conductor and an outer conductor with a dielectric junction (feed point) separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction.

The dipole antenna is connected to a source of microwave energy using a coaxial conductor assembly, the antenna and coaxial feed will be described in more detail below.

In order for such a device to be controlled properly, and to improve the delivery of microwave energy into the tissue being treated, it is desirable for the antenna assembly to be impedance matched with the microwave energy generator. An ablation shape as close to spherical as possible is also desirable. Existing designs of antenna assemblies can be improved upon in these respects.

SUMMARY OF THE INVENTION

According to the present invention, there is provided a microwave ablation antenna assembly comprising an elongate body which extends from a first end to a second end thereof, and which defines therein a hollow inner volume and a longitudinal axis of the antenna; an applicator tip portion mounted on the second end of the elongate body; an elongate coaxial conductor assembly for connection to a source of microwave energy, the coaxial conductor assembly extending from the first end of the body towards the second end of the body through the inner volume, the coaxial conductor assembly having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the coaxial conductor assembly at a distal end thereof towards the second end of the body; a dipole tip portion which extends from the feed point of the coaxial conductor assembly towards the applicator tip, and which is electrically connected with the inner conductor of the coaxial conductor assembly; and a choke assembly comprising a choke dielectric element arranged radially outwardly of the outer conductor of the coaxial conductor, and extending along a part of the outer conductor; a first choke conductor extending around a first portion of the choke dielectric element, radially outwardly thereof, the first choke conductor being electrically connected with the outer conductor of the coaxial conductor; a second choke conductor extending around a second portion of the choke dielectric element, radially outwardly thereof, the second choke conductor being electrically connected with the outer conductor of the coaxial conductor, and being spaced apart longitudinally from the first choke conductor along the coaxial conductor assembly.

Accordingly, embodiments of the present invention may provide improved sphericity of ablation compared to existing designs. Embodiments may also provide improved impedance matching to tissue, minimising power reflected back into the microwave source.

In one example, the first choke conductor extends longitudinally along the coaxial conductor in a direction towards the second choke conductor.

In one example, the first choke conductor is provided by an electrically conductive layer on the choke dielectric element. In one example, the second choke conductor is provided by an electrically conductive layer on the choke dielectric element. In such examples, the or each electrically conductive layer may be of a metallic material.

In one example, the first choke conductor is electrically connected with the outer conductor of the coaxial conductor assembly via a soldered connection. The connection may also be provided by conductive paint, conductive epoxy or other means.

In one example, the second choke conductor is electrically connected with the outer conductor of the coaxial conductor assembly via a soldered connection. The connection may also be provided by conductive paint, conductive epoxy or other means.

In one example, the choke dielectric element is provided by a single continuous member surrounding the part of the outer conductor of the coaxial conductor assembly.

The dielectric element may be of a plastic material or ceramic or other dielectric material In one example, the choke dielectric element is provided by a first and second choke dielectric portions surrounding respective parts of the outer conductor of the coaxial conductor assembly, the first choke dielectric portion being spaced apart from the second choke dielectric portion longitudinally along the coaxial conductor assembly.

In one example, the outer conductor of the coaxial conductor assembly terminates at and end point spaced longitudinally from the feed point of the inner conductor.

In one example, the body is substantially cylindrical, and the coaxial conductor assembly, dipole tip portion and choke assembly are substantially cylindrical and extend substantially centrally through the inner volume of the body.

In one example, a dielectric fluid is provided in the inner volume of the body. Alternatively, the fluid may be a partially conducting dielectric fluid, such as saline or the like, or a dielectric solid.

DETAILED DESCRIPTION OF THE PREFERRED EMBODIMENTS

Figure 1:
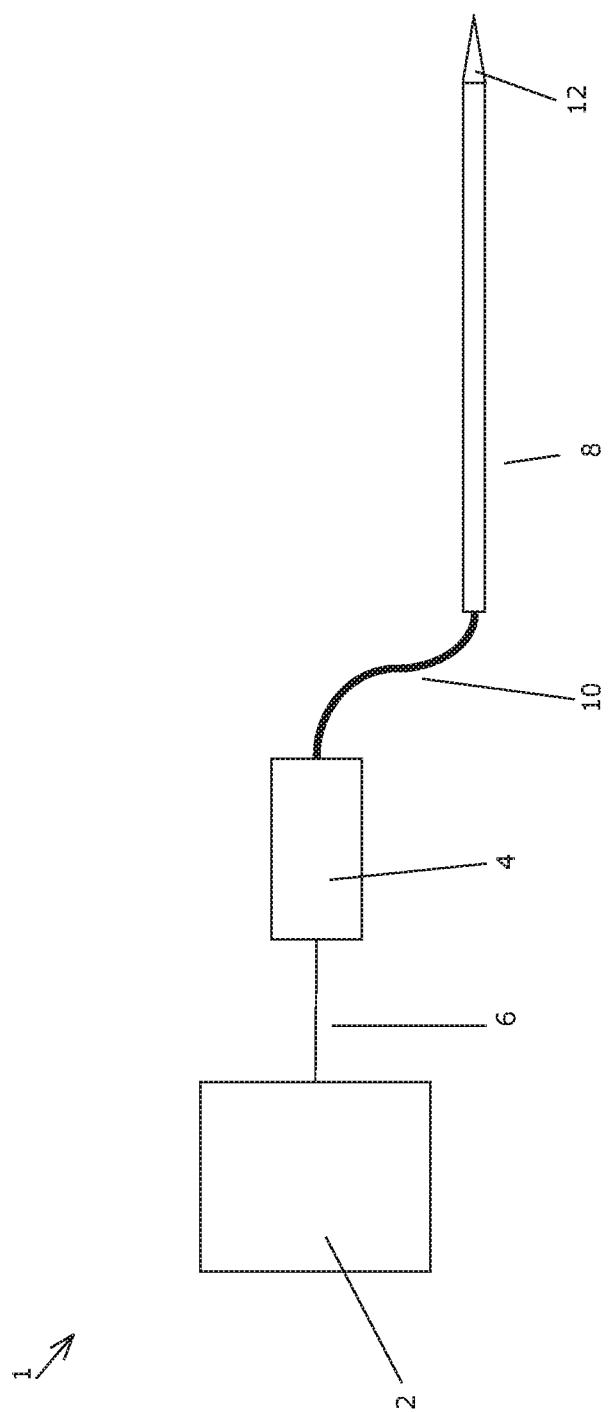
FIG. 1 is a schematic block diagram of a microwave ablation system.

FIG. 1 is a schematic diagram illustrating a microwave ablation system 1 comprising a controller unit 2, and a microwave power generator 4 which is connected to the controller via a control connection 6. An ablation antenna assembly 8 is connected to the microwave power generator 4 via a power connection 10. The antenna assembly includes a tip portion 12 which aids insertion of the antenna assembly into the tissue being treated, and enables a desired output pattern of microwave energy from the antenna assembly.

The controller unit 2 is operable to control the power generator 4 to supply the correct magnitude and frequency of microwave energy to the antenna assembly 8. Different control schemes are known in the art, and will not be described here for the sake of clarity. The present invention is concerned with the design of the antenna assembly, and such an assembly may be used with any appropriate control scheme and control hardware.

Figure 2:
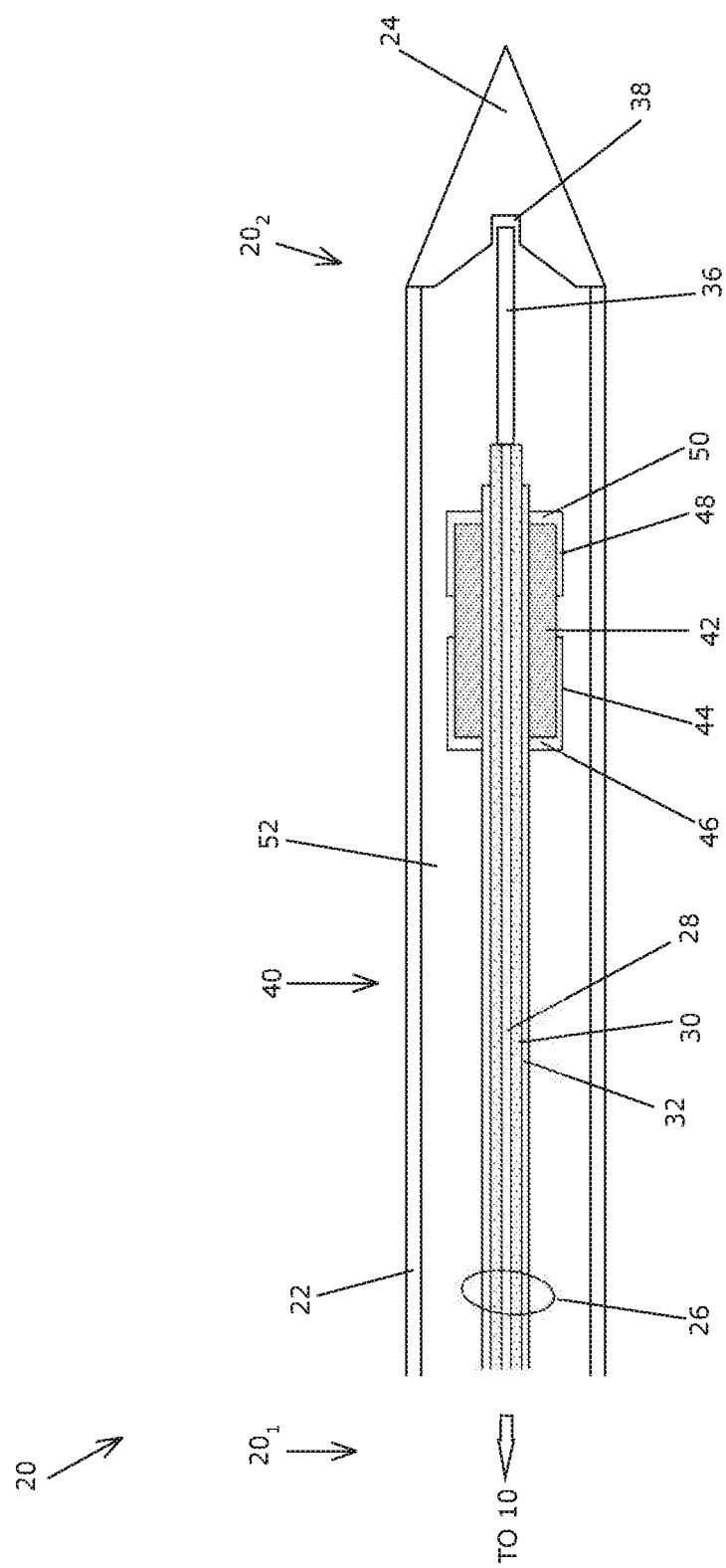
FIG. 2 is a cross sectional view of part of a first microwave ablation antenna assembly embodying the present invention.

FIG. 2 is a cross-sectional view of part of a first antenna assembly 20 embodying the present invention. The antenna assembly 20 comprises a body 22, which is preferably cylindrical in form. The body 22 extends from a first (proximal) end $20_1$ to a second (distal) end $20_2$, and defines a longitudinal axis of the assembly. The body 22 defines an inner volume, in which most of the other components of the assembly are housed. The body 22 provides the assembly with the necessary rigidity for insertion into the tissue being treated. The body 22 is preferably of a rigid material, such as a composite material (for example glass fibre, carbon fibre, aramid fibre), stainless steel, other biocompatible metals (e.g. titanium) or combinations of, and is typically 1.5 to 3 mm in diameter.

An applicator tip 24 is attached to the second end $20_2$ of the body, to close off the inner volume at the second end. The applicator tip is preferably a faceted trocar and has a relatively sharp distal end point. The applicator tip 24 is designed to be suitable for insertion into the tissue being treated, and partly to affect the transmission pattern for microwave energy into that tissue. It also forms a water tight seal to the internal volume of the body 22.

A coaxial conductor assembly 26 extends along the inner volume of the body 22 from the first end $20_1$ towards the second end $20_2$. The coaxial conductor assembly 26 is connectable, at a proximal end thereof, to the microwave energy generator 4 of FIG. 1. The coaxial conductor assembly 26 extends substantially along the longitudinal axis of the body 22, and comprises an inner conductor 28. The inner conductor 28 is of an electrically conductive material such as copper. Surrounding the inner conductor 28 is a dielectric layer 30 which extends along the inner conductor 28, radially outwardly thereof. The dielectric layer 30 is of any appropriate dielectric material. Surrounding the dielectric layer 30, is an outer conductor 32, which is of an electrically conductive material such as copper. The outer conductor 32 extends along the dielectric layer 30, radially outwardly thereof. Typically, the inner conductor 28 is a wire having a circular cross section, such that the dielectric layer 30 is a cylinder of dielectric material surrounding an outer surface of the inner conductor 28. The outer conductor 32 is then formed by a cylinder of electrically conductive material surrounding an outer surface of the dielectric layer 30.

The inner conductor 28 defines a signal feed-point 34 at its distal end (that is, the end towards the second end $20_2$ of the body 22). A dipole tip portion 36 extends longitudinally from the distal end of the coaxial conductor assembly 26 into a reception aperture in the applicator tip 24. The reception aperture 38 is located centrally with respect to the longitudinal axis of the assembly within the applicator tip 24. The reception aperture 38 is designed so as to locate centrally the dipole tip portion 36 into the tip 24. The tip material is chosen for it mechanical and electrical properties, which have to be considered in the design.

The dielectric layer 30 extends along the complete length of the inner conductor 28 to the distal end thereof adjacent the dipole tip portion 36. The outer conductor 32 stops short of the distal end of the inner conductor 28 and dielectric layer 32, and so is spaced apart longitudinally from the signal feed-point 34 and dipole tip portion 36.

A dielectric fluid 52 may be provided within the inner volume of the body 20 in order to provide a key functional element to the microwave design and also provide a cooling fluid for the antenna assembly. This fluid will typically be isotonic saline or deionised water.

Figure 3:
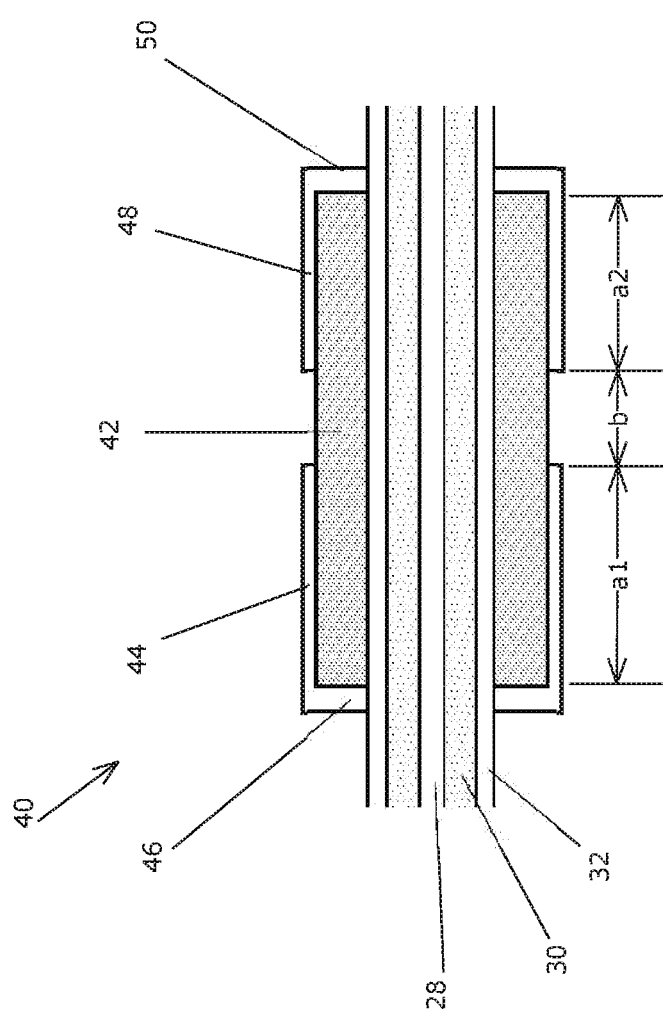
FIG. 3 is a cross sectional view of part of a second microwave ablation antenna assembly embodying the present invention.

A choke assembly 40 is located within the body 22, around the coaxial conductor assembly 26, spaced apart from the distal end of the coaxial conductor assembly 26. The choke assembly is shown in enlarged view in FIG. 3. The choke assembly 40 comprises a choke dielectric element 42 which extends around a portion of the outer conductor 32. In the case when the coaxial conductor assembly 26 has a circular cross section, the choke dielectric element 42 is in the form of a cylinder of dielectric material surrounding an outer surface of the outer conductor 32 of the coaxial conductor assembly 26. The choke dielectric has a proximal end towards the first end $20_1$ of the antenna assembly 20 and a distal end towards the second end $20_2$ of the antenna assembly. The length of the choke dielectric element 42 along the coaxial conductor assembly 26 is determined by the desired electrical characteristics of the choke assembly 40, as will be described below.

A first (proximal) choke conductor 44 extends around a first portion of the choke dielectric element 42. The first choke conductor 44 extends around an outer surface of the choke dielectric element 42, from the proximal end of the element 42, partially along the element 42 towards the distal end of the element 42. The internal length a1 of the first choke conductor 44 (that is the portion of the first conductor that overlaps the choke dielectric element 42) is determined by the required electrical properties of the choke assembly 40. The internal length a1 is chosen so the wavelength of an electromagnetic wave travelling from the distal tip has a round trip distance of $\lambda/2$ within the choke dielectric. $\lambda$ being the wavelength of the microwave energy. This has the effect of cancelling electromagnetic energy from the tip and preventing a 'teardrop' energy pattern caused by the coaxial conductor assembly 26 acting as a monopole antenna. This will result in a more spherical ablation pattern. In a preferred embodiment, the first choke conductor 44 is provided by an electrically conductive layer deposited or plated on the outer surface of the choke dielectric element 42. Such a layer is preferably metallic, for example copper.

The first choke conductor 44 is electrically connected with the outer conductor 32 of the coaxial conductor assembly 26 by a first choke connector 46. The first choke connector 46 may be provided by any suitable means, such as a soldered connection, or by an electrically conductive collar, for example of copper. The first choke connector 46 may be provided by conductive paint, conductive epoxy or other means.

A second choke conductor 48 extends around a second portion of the choke dielectric element 42. The second choke conductor 48 extends around an outer surface of the choke dielectric element 42, from the distal end of the element 42, partially along the element 42 towards the proximal end of the element 42. The internal length a2 of the second choke conductor 44 is determined so as to broadly define a distance of λ/4 from the distal termination of the conductive layer to the feed point. This path forming the proximal leg of the dipole antenna. In this instance λ will be that for the dielectric fluid 52. In a preferred embodiment, the second choke conductor 48 is provided by an electrically conductive layer deposited or plated on the outer surface of the choke dielectric element 42. Such a layer is preferably metallic, for example copper.

The second choke conductor 48 is electrically connected with the outer conductor 32 of the coaxial conductor assembly 26 by a second choke connector 50. The second choke connector 50 may be provided by any suitable means, such as a soldered connection, or by an electrically conductive collar, for example of copper. The second choke connector may be provided by conductive paint, conductive epoxy or other means.

The first and second choke conductors 44 and 48 extend towards one another and are spaced apart from one another in a central region of the choke dielectric element 42. The spacing b of the first and second choke conductors 44 and 48 is determined by overall performance of the choke assembly 40.

In general, the first and second choke conductors will not have the same internal lengths a1 and a2. Although both internal lengths a1 and a2 are substantially equal to λ/4, the internal length a1 of the first choke conductor 44 is defined by the microwave wavelength in the choke dielectric element 42, whilst the internal length a2 of the second choke conductor 48 is defined by the microwave wavelength in the dielectric fluid 52. In general, the dielectric fluid 52 has a higher permittivity than the choke dielectric element 42, and consequently a shorter microwave wavelength.

The wavelength of an electromagnetic wave, such as a microwave, is given by:

$$\lambda_0 * \frac{1}{\sqrt{\epsilon_r}}$$

where $\lambda_0$ is the microwave wavelength in a vacuum, and $\epsilon\_r$ is the relative permittivity of the choke dielectric element 42.

The internal length a1 of the first choke conductor 44 is equal to λ/4, where λ is the microwave wavelength in the choke dielectric element 42.

In one example, in which the choke dielectric element 42 is of zirconia, for a microwave frequency of 2.45 GHz, the internal length a1 of the first choke conductor 44 is approximately 5.5 mm.

In another example, in which the choke dielectric element 42 is of a plastics material such as polyamide, for a microwave frequency of 2.45 GHz, the internal length a1 of the first choke conductor 44 is approximately 16 mm.

The surface distance from the feed point to the cessation of the metal of the distal choke forms one arm of the radiating dipole and will therefore be approximately equal to λ/4. The wavelength will be modified in a similar manner to above. This time ∈r will be that for saline or water, and equal approximately to 70. λ/4 will in this case be approximately equal to 3.5 mm, though in practice the effective permittivity will be influenced by the surrounding tissue as well, which is of lower permittivity. Accordingly, the internal length a2 of the second choke conductor will be modified upwards.

Figure 4:
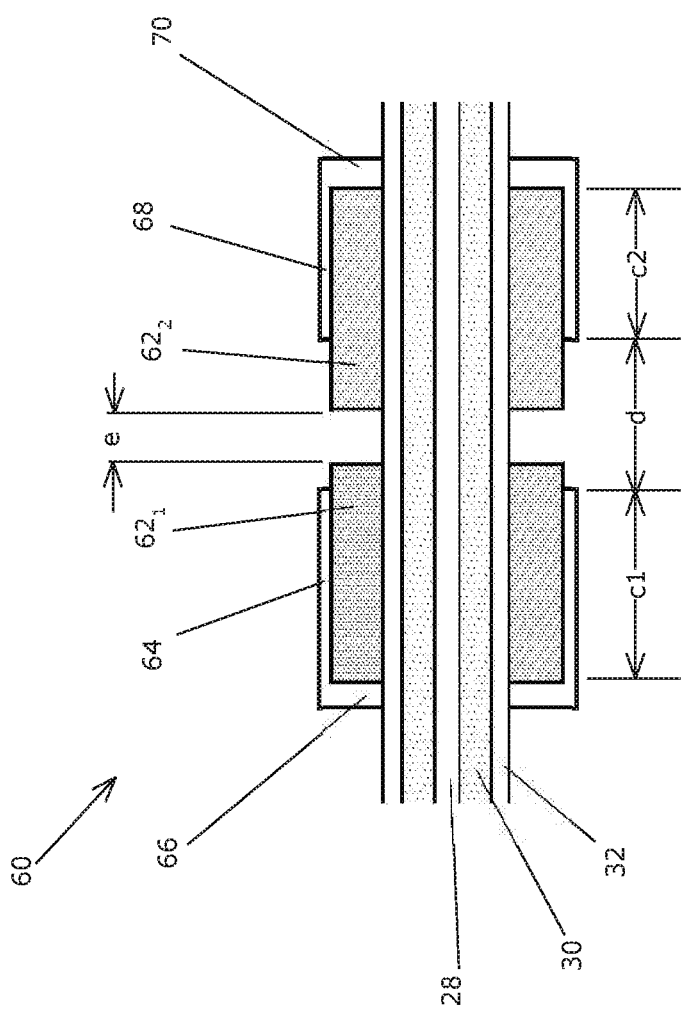
FIG. 4 is a cross sectional view of part of a third microwave ablation antenna assembly embodying the present invention.

FIG. 4 shows an enlarged view of an alternative choke assembly 60, for use in a microwave ablation antenna assembly embodying the present invention.

As before, the choke assembly 60 is located within the body, around the coaxial conductor assembly 26, spaced apart from the distal end of the coaxial conductor assembly 26. The choke assembly 60 comprises first and second choke dielectric elements $62_1$ and $62_2$ which extend around respective portions of the outer conductor 32. In the case when the coaxial conductor assembly 26 has a circular cross section, the choke dielectric elements $62_1$ and $62_2$ are in the form of cylinders of dielectric material surrounding an outer surface of the outer conductor 32 of the coaxial conductor assembly 26. The first choke dielectric element $62_1$ has a proximal end towards the first end $20_1$ of the antenna assembly 20 and a distal end towards the second end $20_2$ of the antenna assembly. Similarly, the second choke dielectric element $62_2$ has a proximal end towards the first end $20_1$ of the antenna assembly 20 and a distal end towards the second end $20_2$ of the antenna assembly. The second choke dielectric element $62_2$ is spaced apart along the coaxial conductor assembly 26 from the first choke dielectric element $62_1$ by a distance e.

The respective lengths of the first and second choke dielectric elements $62_1$ and $62_2$ along the coaxial conductor assembly 26 are determined by the desired electrical characteristics of the choke assembly 60, as will be described below.

A first choke conductor 64 extends around a first portion $62_1$ of the choke dielectric element 62. The first choke conductor 64 extends around an outer surface of the choke dielectric element 62, from the proximal end of the element 62, partially along the element 62 towards the distal end of the element 62. The length c1 of the first choke conductor 64 is determined so as to optimise the ablation shape from the antenna. In a preferred embodiment, the first choke conductor 64 is provided by an electrically conductive layer deposited or plated on the outer surface of the choke dielectric element 62. Such a layer is preferably metallic, for example copper.

The first choke conductor 64 is electrically connected with the outer conductor 32 of the coaxial conductor assembly 26 by a first choke connector 66. The first choke connector 66 may be provided by any suitable means, such as a soldered connection, conductive paint or epoxy, or by an electrically conductive collar, for example of copper.

A second choke conductor 68 extends around a second portion of the choke dielectric element 62 and includes a second choke connector 70. The second choke conductor 68 extends around an outer surface of the choke dielectric element 62, from the distal end of the element 62, partially along the element 62 towards the proximal end of the element 62. The length c2 of the second choke conductor 68 is determined so as to optimise the antenna performance as a dipole radiator and also to optimise the impedance presented to the microwave source. In a preferred embodiment, the second choke conductor 68 is provided by an electrically conductive layer deposited or plated on the outer surface of the choke dielectric element 62. Such a layer is preferably metallic, for example copper.

The second choke conductor 68 is electrically connected with the outer conductor 32 of the coaxial conductor assembly 26 by a second choke connector 50. The second choke connector 50 may be provided by any suitable means, such as a soldered connection, conductive paint or epoxy, or by an electrically conductive collar, for example of copper.

The first and second choke conductors 64 and 68 extend towards one another and are spaced apart from one another in a central region of the choke dielectric element 62. The spacing d of the first and second choke conductors 64 and 68 is determined by the required properties of the choke assembly 60.

In general, the first and second choke conductors 64 and 68 will not have the same internal lengths c1 and c2. Although both internal lengths c1 and c2 are substantially equal to $\lambda/4$, the internal length c1 of the first choke conductor 64 is defined by the microwave wavelength in the choke dielectric element $62_1$, whilst the internal length c2 of the second choke conductor 68 is defined by the microwave wavelength in the dielectric fluid 52. In general, the dielectric fluid 52 has a higher permittivity than the choke dielectric element $62_1$, and consequently a shorter microwave wavelength.

The internal length c1 of the first choke conductor 64 is equal to $\lambda/4$, where $\lambda$ is the microwave wavelength in the choke dielectric element $62_1$.

In one example, in which the choke dielectric element $62_1$ is of zirconia, for a microwave frequency of 2.45 GHz, the internal length c1 of the first choke conductor 64 is approximately 5.5 mm.

In another example, in which the choke dielectric element $62_1$ is of a plastics material such as polyamide, for a microwave frequency of 2.45 GHz, the internal length a1 of the first choke conductor 24 is approximately 16 mm.

The surface distance from the feed point to the cessation of the metal of the second choke conductor forms one arm of the radiating dipole and will therefore be approximately equal to $\lambda/4$. The wavelength will be modified in a similar manner to above. This time ∈r will be that for saline or water, and equal approximately to 70. $\lambda/4$ will in this case be approximately equal to 3.5 mm, though in practice the effective permittivity will be influenced by the surrounding tissue as well, which is of lower permittivity. Accordingly, the internal length c2 of the second choke conductor will be modified upwards.

A microwave ablation antenna assembly embodying the present invention is able to provide improved performance when compared to previously-considered designs in the following manner. Compared to antennas without a choke, the shape of the ablation is more spherical, allowing the improved treatment of tumours without damage to adjacent tissue proximal to the treatment area. Such an improvement is provided by the novel design of choke assembly as described above. The choke designs described provide improved impedance matching by virtue of the dielectric buffering effect of the surrounding dielectric fluid, which makes the surrounding tissue less important in determining the impedance presented to the source. This improves the matching between the antenna assembly and the microwave energy generator, thereby improving the efficiency of transfer of microwave energy from the generator to the antenna assembly, and on to the tissue being treated. This improved matching allows the treatment of a range of body tissues of differing electrical characteristics with the same applicator. It also means that over the duration of a treatment changes in the tissue as it is ablated do no cause poor energy transfer to the tissue. High reflected power also causes heating of associated cables and connectors, power dissipated in the source and the need for higher source power.

What is claimed is:

1. A microwave ablation antenna assembly comprising:
   an elongate body which extends from a first end to a second end thereof, and which defines therein a hollow inner volume and a longitudinal axis of the microwave ablation antenna;
   an applicator tip portion mounted on the second end of the elongate body;
   an elongate coaxial conductor assembly for connection to a source of microwave energy, the elongate coaxial conductor assembly having a circular cross-section and extending from the first end of the elongate body towards the second end of the elongate body through the hollow inner volume, the elongate coaxial conductor assembly having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the elongate coaxial conductor assembly at a distal end thereof towards the second end of the elongate body;
   a dipole tip portion which extends from the signal feed-point of the elongate coaxial conductor assembly towards the applicator tip portion, and which is electrically connected with the inner conductor of the elongate coaxial conductor assembly; and
   a choke assembly comprising:
     a choke dielectric element comprising a cylinder of solid dielectric material arranged radially outwardly of the outer conductor of the elongate coaxial conductor assembly, and extending along a part of the outer conductor;
     a first choke conductor extending along, around and adjacent to a first portion of the choke dielectric element, radially outwardly thereof, the first choke conductor being electrically connected with the outer conductor of the elongate coaxial conductor assembly; and
     a second choke conductor extending along, around and adjacent to a second portion of the choke dielectric element, radially outwardly thereof, the second choke conductor being electrically connected with the outer conductor of the elongate coaxial conductor assembly, and being spaced apart longitudinally from the first choke conductor along the elongate coaxial conductor assembly; and
   a second dielectric element arranged radially outwardly of the first and second choke conductors and the choke dielectric element and extending over and along the first and second choke conductors and is in direct contact with a portion of the choke dielectric element located between the first and second choke conductors, but not in direct contact with any other part of the choke dielectric element, and wherein the second dielectric element extends along and around the dipole tip portion.

2. The microwave ablation antenna assembly as claimed in claim 1, wherein the first choke conductor is provided by an electrically conductive layer on the choke dielectric element.

3. The microwave ablation antenna assembly as claimed in claim 1, wherein the second choke conductor is provided by an electrically conductive layer on the choke dielectric element.

4. The microwave ablation antenna assembly as claimed in claim 2, wherein the electrically conductive layer on the choke dielectric element comprises a metallic material.

5. The microwave ablation antenna assembly as claimed in claim 1, wherein the first choke conductor is electrically connected with the outer conductor of the elongate coaxial conductor assembly via a soldered connection conductive paint, or conductive epoxy.

6. The microwave ablation antenna assembly as claimed in claim 1, wherein the second choke conductor is electrically connected with the outer conductor of the elongate coaxial conductor assembly via a soldered connection, conductive paint, or conductive epoxy.

7. The microwave ablation antenna assembly as claimed in claim 1, wherein the choke dielectric element is provided by a single continuous member surrounding the part of the outer conductor of the elongate coaxial conductor assembly.

8. The microwave ablation antenna assembly as claimed in claim 1, wherein the outer conductor of the elongate coaxial conductor assembly terminates at an end point spaced longitudinally from the signal feed-point of the inner conductor.

9. The microwave ablation antenna assembly as claimed in claim 1, wherein the elongate body is cylindrical, and the elongate coaxial conductor assembly, the dipole tip portion and the choke assembly extend substantially centrally through the hollow inner volume of the elongate body.

10. The microwave ablation antenna assembly as claimed in claim 1, further comprising a dielectric fluid in the hollow inner volume of the elongate body.

11. The microwave ablation antenna assembly as claimed in claim 1, wherein the second dielectric element comprises a fluid dielectric material.

\* \* \* \* \*